US010450425B2

(12) United States Patent
Nam et al.

(10) Patent No.: US 10,450,425 B2
(45) Date of Patent: Oct. 22, 2019

(54) SUPER ABSORBENT POLYMER AND METHOD FOR PREPARING THE SAME

(71) Applicant: LG Chem, Ltd., Seoul (KR)

(72) Inventors: Hye Mi Nam, Daejeon (KR); Sang Gi Lee, Daejeon (KR); Tae Hwan Jang, Daejeon (KR); Min Ho Hwang, Daejeon (KR); Soo Jin Lee, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/107,297

(22) PCT Filed: Nov. 11, 2015

(86) PCT No.: PCT/KR2015/012121
§ 371 (c)(1),
(2) Date: Jun. 22, 2016

(87) PCT Pub. No.: WO2016/085163
PCT Pub. Date: Jun. 2, 2016

(65) Prior Publication Data
US 2017/0009026 A1 Jan. 12, 2017

(30) Foreign Application Priority Data
Nov. 24, 2014 (KR) .................. 10-2014-0164520

(51) Int. Cl.
| *C08J 3/12* | (2006.01) |
| *C08J 3/075* | (2006.01) |
| *B02C 18/36* | (2006.01) |
| *C08F 220/06* | (2006.01) |
| *C08J 3/24* | (2006.01) |
| *A61L 15/60* | (2006.01) |

(52) U.S. Cl.
CPC ................ *C08J 3/12* (2013.01); *A61L 15/60* (2013.01); *B02C 18/365* (2013.01); *C08F 220/06* (2013.01); *C08J 3/075* (2013.01); *C08J 3/245* (2013.01); *C08F 2800/20* (2013.01); *C08F 2810/20* (2013.01); *C08J 2300/14* (2013.01); *C08J 2333/02* (2013.01)

(58) Field of Classification Search
CPC .... C08J 3/12; C08J 3/245; C08J 3/075; A61L 15/60; C08F 220/06; C08F 20/06
See application file for complete search history.

(56) References Cited

U.S. PATENT DOCUMENTS

| 4,446,261 A | 5/1984 | Yamasaki et al. |
| 5,837,789 A | 11/1998 | Stockhausen et al. |
| 6,133,193 A | 10/2000 | Kajikawa et al. |
| 2004/0077557 A1 | 4/2004 | Ali et al. |
| 2007/0066167 A1 | 3/2007 | Wada et al. |
| 2007/0207924 A1 | 9/2007 | Ikeuchi et al. |
| 2009/0131255 A1 | 5/2009 | Ikeuchi et al. |
| 2009/0239966 A1 | 9/2009 | Matsumoto et al. |
| 2011/0003926 A1 | 1/2011 | Nogi et al. |
| 2011/0290920 A1 | 12/2011 | Kim et al. |
| 2011/0301303 A1 | 12/2011 | Kim et al. |
| 2015/0087742 A1 | 3/2015 | Won et al. |

FOREIGN PATENT DOCUMENTS

| CN | 1709980 A | 12/2005 |
| CN | 101072817 A | 11/2007 |
| GB | 2119384 | * 11/1983 |
| JP | 56161408 A | 12/1981 |
| JP | 57158209 A | 9/1982 |
| JP | 57198714 A | 12/1982 |
| JP | 2001-79829 | * 3/2001 |
| JP | 2005097593 A | 4/2005 |
| JP | 4132592 B2 | 8/2008 |
| JP | 2009509723 A | 3/2009 |
| JP | 2014512440 A | 5/2014 |
| JP | 05524042 B2 | 6/2014 |
| KR | 100269980 B1 | 10/2000 |
| KR | 1020030068189 A | 8/2003 |
| KR | 1020070007162 A | 1/2007 |
| KR | 1020070012623 A | 1/2007 |
| KR | 1020110134333 A | 12/2011 |
| KR | 101114966 B1 | 2/2012 |
| KR | 1020130120400 A | 11/2013 |
| KR | 1020140126280 A | 10/2014 |
| KR | 1020140134219 A | 11/2014 |
| WO | 9216565 A1 | 10/1992 |
| WO | 9305080 A1 | 3/1993 |
| WO | 9321237 A1 | 10/1993 |
| WO | WO 93/21237 | * 10/1993 |
| WO | 9419377 A1 | 9/1994 |
| WO | 9505856 A1 | 3/1995 |

OTHER PUBLICATIONS

JP 2001-79829, Mar. 2001, machine translation.*
UV Coatings: Basics, Recent Developments and New Application (Elsevier 2007), p. 115.
Principle of Polymerization (Wiley, 1981), p. 203.
International Search Report for Application No. PCT/KR2015/012121 dated Feb. 29, 2016.
Third Party Observation for Application No. PCT/KR2015/012121 dated Mar. 23, 2017.

* cited by examiner

*Primary Examiner* — Roberto Rabago
(74) *Attorney, Agent, or Firm* — Lerner, David, Littenberg, Krumholz & Mentlik, LLP

(57) ABSTRACT

The present invention relates to a super absorbent polymer and a method for preparing the same. The present invention has features that it is possible to prepare a super absorbent resin that can have an improved centrifuge retention capacity (CRC) and a high absorbency under load (AUL) by controlling the shape and size of the chopper die holes during coarse pulverization of a hydrous gel phase polymer.

11 Claims, 4 Drawing Sheets

[FIG. 1]
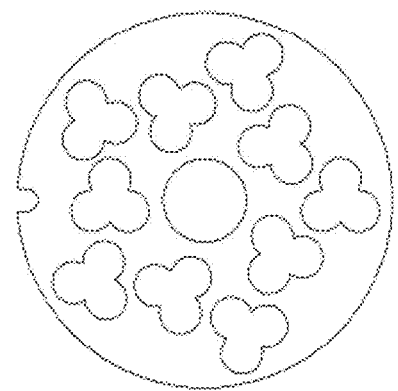
[FIG. 2]
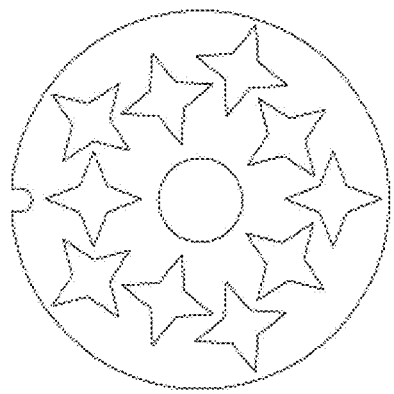

[FIG. 3]
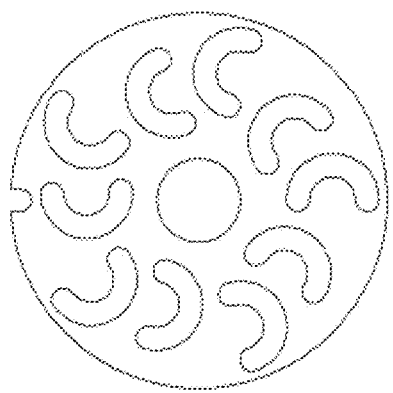
[FIG. 4]
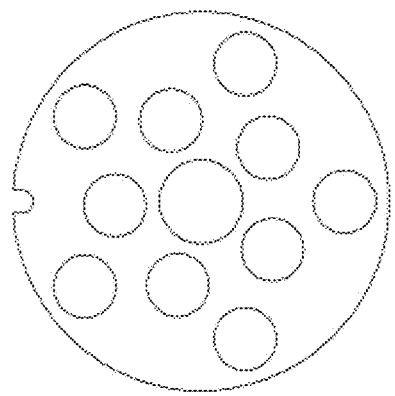

[FIG. 5]
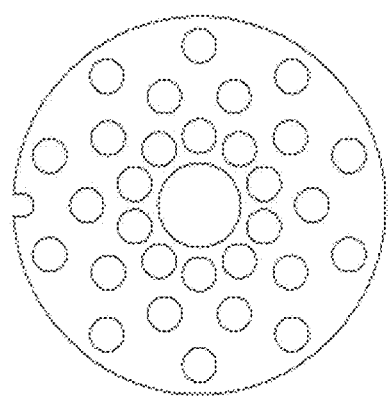

[FIG. 6]
(a)
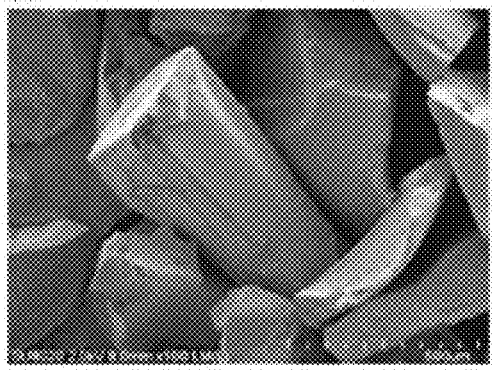
(b)
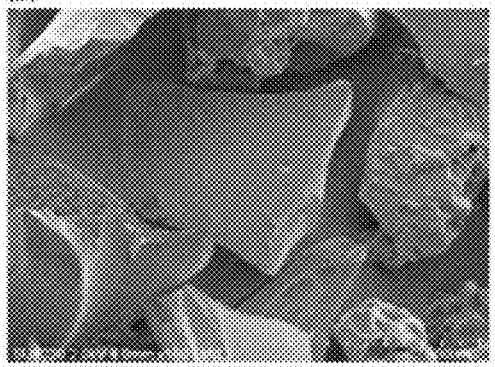
(c)
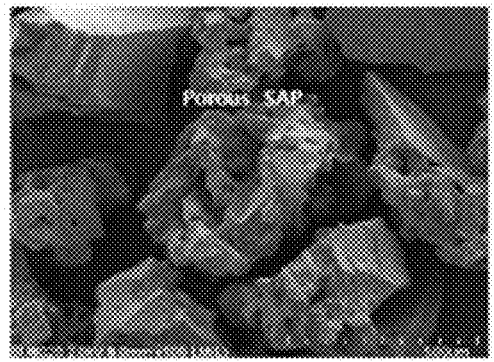
(d)
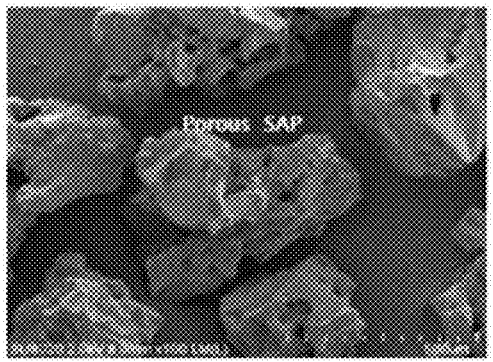

SUPER ABSORBENT POLYMER AND METHOD FOR PREPARING THE SAME

CROSS-REFERENCE TO RELATED APPLICATION(S)

The present application is a national phase entry under U.S.C. § 371 of International Application No. PCT/KR2015/012121, filed Nov. 11, 2015, which claims priority from Korean Patent Application No. 10-2014-0164520 filed, Nov. 24, 2014, all of which are incorporated herein by reference.

TECHNICAL FIELD

The present invention relates to a super absorbent polymer which has fast absorption rate and high absorbency under load, and a method for preparing the same.

BACKGROUND OF ART

Super absorbent polymer (SAP) is a synthetic polymer material capable of absorbing moisture from about 500 to about 1,000 times its own weight, and it has been also called a super absorbency material (SAM), an absorbent gel material (AGM) and so on. Such super absorbent polymers started to be practically applied in sanitary products, and now they are widely used for preparation of various products, for example, hygiene products such as disposable diapers for children, water retaining soil products for gardening, water stop materials for the civil engineering and construction, sheets for raising seedling, fresh-keeping agents for food distribution fields, or the like.

As a method for preparing such a super absorbent polymer, an inverse suspension polymerization method, an aqueous solution polymerization method or the like are known. Among them, the preparation of super absorbent polymers via inverse suspension polymerization is disclosed in Japanese Patent Publication Nos. Sho56-161408, Sho57-158209, Sho57-198714, and so on. Furthermore, for the preparation of super absorbent polymers via aqueous solution polymerization, a thermal polymerization method of polymerizing a hydrous gel phase polymer while breaking and cooling the same in a kneader equipped with a plurality of spindles, and a photo-polymerization method of exposing a high-concentrated aqueous solution to UV rays or the like on a belt so as to carry out the polymerization and drying at the same time are known.

On the other hand, the absorption rate, one of important physical properties of super absorbent polymers is associated with the surface dryness of the product in contact with a skin, such as disposable diapers. In general, these absorption rates can be improved in a manner of widening a surface area of the super absorbent polymer.

As an example, a method in which a porous structure is formed on the particle surface of the super absorbent polymer by using a blowing agent has been applied. However, general blowing agents have a disadvantage that a sufficient amount of the porous structure cannot be formed and thus the absorption rate is not highly increased.

As another example, there is a method for increasing a surface area of the super absorbent polymer by reassembling fine particles obtained during preparation of the super absorbent polymer to form a porous particle with irregular shape. However, although the absorption rate of the super absorbent polymer can be improved through these methods, there is a limit that a centrifuge retention capacity (CRC) and an absorbency under load (AUL) of the polymer are relatively decreased. In this way, because physical properties such as an absorption rate, a retention capacity, an absorbency under load of the super absorbent polymer have a trade-off relation, there is an urgent need for the preparation method capable of improving these properties simultaneously.

DETAILED DESCRIPTION OF THE INVENTION

Technical Problem

For resolving the aforesaid problems of the prior arts, it is an object of the present invention to provide a method for preparing a super absorbent polymer that has an improved centrifuge retention capacity (CRC), a high absorbency under load (AUL) and a ratio of the absorbency under load at 5 minutes to the absorption under load at 60 minutes (ARUL) by controlling the shape and size of the chopper die holes during coarse pulverization of a hydrous gel phase polymer.

Technical Solution

To achieve the above object, the present invention provides a super absorbent polymer comprising a crosslinked polymer, the crosslinked polymer being obtained by surface-crosslinking a base polymer prepared by polymerizing a water-soluble ethylene-based unsaturated monomer including an acidic group in which at least a part of the acidic group is neutralized, wherein the super absorbent polymer has a centrifuge retention capacity (CRC) of more than 20 g/g, an absorbency under 0.9 psi load (AUL) of more than 18 g/g, and ARUL shown in the following Equation 1 of 60% to 85%:

$$\text{ARUL} = 0.3\text{AUL}(5 \text{ min})/0.3\text{AUL}(60 \text{ min}) \quad \text{[Equation 1]}$$

in Equation 1, 0.3AUL (5 min) and 0.3AUL (60 min) are the values of absorbency under load (AUL) at 5 minutes and 60 minutes shown in the following Equation 2, respectively, $$0.3\text{AUL}(g/g) = [Wb(g) - Wa(g)]/\text{weight}(g) \text{ of the absorbent polymer} \quad \text{[Equation 2]}$$

in Equation 2,

Wa(g) is the sum of the weight of the absorbent polymer and the weight of the device capable of providing a load for the absorbent polymer, and Wb(g) is the sum of the weight of the absorbent polymer in which moisture is absorbed after supplying water for the absorbent polymer under a load (0.3 psi) for 5 minutes or 60 minutes, and the weight of the device capable of providing a load for the absorbent polymer.

As described above, the super absorbent polymers according to the present invention have not only excellent centrifuge retention capacity (CRC) and absorbency under load (AUL) but also excellent ratio of the absorbency under load at 5 minutes to the absorbency under pressure at 60 minutes (ARUL).

The water-soluble ethylene-based unsaturated monomer included in the monomer composition may be any monomer that is generally used in the preparation of the super absorbent polymer. In one non-limiting example, the water-soluble ethylene-based unsaturated monomer may be a compound represented by the following Chemical Formula 1:

$$R_1\text{-COOM}^1 \quad \text{[Chemical Formula 1]}$$

in Chemical Formula 1, $R_1$ is a $C_2$-$C_5$ alkyl group including an unsaturated bond, and $M^1$ is a hydrogen atom, a monovalent or divalent metal, an ammonium group, or an organic amine salt.

Preferably, the above-mentioned monomers may be one or more selected from the group consisting of acrylic acid, methacrylic acid, and monovalent or divalent metal salts of these acids, ammonium salts and organic amine salts.

Thus, when using acrylic acid or a salt thereof as the water-soluble ethylene-based unsaturated monomer as described above, it is advantageous because the super absorbent polymer having improved water absorption properties can be obtained. In addition, as the monomers, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, (meth) acrylamide, N-substituted (meth)acrylate, 2-hydroxyethyl (meth)acrylate, 2-hydroxypropyl (meth)acrylate, methoxypolyethyleneglycol (meth)acrylate, polyethyleneglycol (meth)acrylate; (N,N)-dimethylaminoethyl(meth)acrylate, (N,N)-dimethylaminopropyl (meth)acrylamide, and the like may be used.

Here, the water-soluble ethylene-based unsaturated monomer may have an acidic group in which at least a part of the acidic group is neutralized. Preferably, the monomers that are used herein may include those partially neutralized with an alkaline substance such as sodium hydroxide, potassium hydroxide or ammonium hydroxide.

In this case, the degree of neutralization of the monomer may be 40 to 95 mol %, or 40 to 80 mol %, or 45 to 75 mol %. The range of the degree of neutralization may vary depending on the final physical properties. However, if the degree of neutralization is too high, the neutralized monomer may be precipitated and thus it may be difficult to perform polymerization smoothly. In contrast, if the degree of neutralization is too low, the absorptive capacity of the polymer is greatly reduced and also it may exhibit elastic rubber-like properties which are difficult-to-handle.

Further, the concentration of the water-soluble ethylene-based unsaturated monomer in the monomer composition may be appropriately controlled considering a polymerization time, a reaction condition and the like, and it may be preferably 20 to 90% by weights or 40 to 65% by weights. The concentrations may have advantageous range to control the pulverizing efficiency during the pulverization of the polymer which will be described later, while eliminating the necessity of removing non-reacted monomers after polymerization using a gel effect phenomenon that appears in the polymerization reaction of high-concentration aqueous solutions. However, if the concentration of the monomer is too low, the yield of the super absorbent polymer may be decreased. In contrast, if the concentration of the monomer is too high, there may be a process problem that a part of the monomers may be precipitated or pulverization efficiency may be lowered upon pulverization of the polymerized hydrous gel phase polymer, and the physical properties of the super absorbent polymer may be degraded.

The surface crosslinking is a method for increasing the crosslinking density near the surface of the polymer particles, and the crosslinking agent and the surface crosslinking method used herein will be described later.

Meanwhile, the absorbency under 0.9 psi load (AUL) can be represented by the following Equation 3:

$$0.9\text{AUL}(g/g) = [Wb(g) - Wa(g)]/\text{weight}(g) \text{ of the absorbent polymer} \qquad \text{[Equation 3]}$$

in Equation 3,

Wa(g) is the sum (g) of the weight of the absorbent polymer and the weight of the device capable of providing a load for the absorbent polymer, and Wb(g) is the sum (g) of the weight of the absorbent polymer in which moisture is absorbed after supplying water for the absorbent polymer under a load (0.9 psi) for 60 minutes, and the weight of the device capable of providing a load for the absorbent polymer.

Also, the centrifuge retention capacity (CRC) can be represented by the following Equation 4:

$$\text{CRC}(g/g) = \{[W_2(g) - W_1(g)]/W_0(g)\} - 1 \qquad \text{[Equation 4]}$$

in Equation 4, $W_0(g)$ is a weight (g) of the absorbent polymer, $W_1(g)$ is a weight (g) of the device which is measured after draining water off at 250 G for 3 minutes with a centrifuge, without using the absorbent polymer, and $W_2(g)$ is a weight (g) of the device including the absorbent polymer, which is measured after immersing the absorbent polymer in 0.9% by weight of the physiological saline solution at room temperature for 30 minutes and then draining water off at 250 G for 3 minutes with a centrifuge.

Method for Preparing a Super Absorbent Polymer

The super absorbent polymer according to the present invention can be prepared by a method comprising the steps of:

1) carrying out thermal polymerization or photopolymerization of a monomer composition including a water-soluble ethylene-based unsaturated monomer and a polymerization initiator to form a hydrous gel phase polymer;

2) passing the hydrous gel phase polymer through a chopper die and pulverizing the polymer;

3) drying the pulverized hydrous gel phase polymer;

4) pulverizing the dried polymer; and 5) surface-crosslinking the pulverized polymer, wherein the chopper die is provided with a plurality of holes, the chopper die has an opening/closing rate of 30 to 40%, and the chopper die satisfies the following Mathematical Formula 1:

$$c > 2 \times \sqrt{0.4 \times \pi \times n \times A} \qquad \text{[Mathematical Formula 1]}$$

wherein

A is the overall area of the upper surface of the chopper die, n is the number of holes, and c is the total circumference of the plurality of holes.

The super absorbent polymer is prepared by a method of polymerizing a hydrous gel phase polymer, followed by drying, pulverizing and surface-crosslining, wherein a step of coarsely pulverizing the polymerized hydrous gel phase polymer is further included between the polymerization and the drying.

The coarsely pulverizing step can not only increase the efficiency of drying but also affect the morphology of the super absorbent polymer depending on the coarsely pulverizing method, thus affecting a centrifuge retention capacity (CRC) and an absorbency under load (AUL) of the super absorbent polymer. Thus, the present invention has a feature that a centrifuge retention capacity (CRC) and an absorbency under load (AUL) of the super absorbent polymer are improved by changing the hole shape into another non-circular shape in the step of passing the hydrous gel phase polymer through the chopper die having a plurality of holes to coarsely pulverize it.

It will now be described in detail step by step for the present invention.

Step of Forming a Hydrous Gel Phase Polymer (Step 1)

First, the method for preparing the super absorbent polymer includes a step of carrying out thermal polymerization or photopolymerization of a monomer composition including a water-soluble ethylene-based unsaturated monomer and a polymerization initiator to form a hydrous gel phase polymer.

The water-soluble ethylene-based unsaturated monomer included in the monomer composition is as previously described.

Also, the monomer composition may include a polymerization initiator that is generally used in the preparation of the super absorbent polymer. In one non-limiting example, the polymerization initiator that can be used herein includes a thermal polymerization initiator or a photopolymerization initiator, depending on the polymerization method. However, even in the case of using the photopolymerization method, because a certain amount of heat is generated by the ultraviolet irradiation or the like and a certain degree of heat is generated according to the progress of the polymerization reaction, i.e., exothermic reaction, a thermal polymerization initiator may be additionally included.

Here, the photopolymerization initiator, for example, may include one or more compounds selected from the group consisting of a benzoin ether, a dialkyl acetophenone, a hydroxyl alkylketone, a phenyl glyoxylate, a benzyl dimethyl ketal, an acyl phosphine, and an α-aminoketone. Among them, specific examples of the acyl phosphine may include normal lucirin TPO, namely, 2,4,6-trimethyl-benzoyl-trimethyl phosphine oxide. More various photopolymerization initiators are disclosed in "UV Coatings: Basics, Recent Developments and New Application (Elsevier, 2007), p 115," written by Reinhold Schwalm, which is herein incorporated by reference.

And, as the thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like. Also, examples of the azo-based initiator may include 2,2-azobis(2-amidinopropane)dihydrochloride, 2,2-azobis-(N,N-dimethylene)isobutyramidine dihydrochloride; 2-(carbamoylazo)isobutylonitrile, 2,2-azobis[2-(2-imidazolin-2-yl)propane] dihydrochloride, 4,4-azobis-(4-cyanovaleric acid) and the like. More various thermal polymerization initiators are disclosed in "Principle of Polymerization (Wiley, 1981), p 203" written by Odian, which is herein incorporated by reference.

These polymerization initiators may be included in the concentration of about 0.001% to 1% by weight based on the monomer composition. That is, when the concentration of the polymerization initiator is too low, the polymerization rate may become slow and residual monomer in the final product can be extracted in a large amount, which is not preferable. In contrast, when the concentration of the photopolymerization initiator is too high, physical properties of the polymer may be deteriorated, for example, the polymer chain forming a network is shortened, the content of water-soluble component is increased and the absorbency under load is lowered, which is not preferable.

Meanwhile, the monomer composition may further include a crosslinking agent ("internal crosslinking agent") in order to improve physical properties of the polymer by the polymerization of the water-soluble ethylene-based unsaturated monomer. The crosslinking agent is for the internal crosslinking of the hydrous gel phase polymer and it can be used separately from a crosslinking agent for crosslinking the surface of the hydrous gel phase polymer ("surface crosslinking agent").

As the internal crosslinking agent, any compound can be used as long as it allows the formation of the crosslinking during polymerization of the water-soluble ethylene-based unsaturated monomer. In non-limiting examples of the internal crosslinking agent, polyfunctional crosslinking agents such as N,N'-methylenebisacrylamide, trimethylolpropane tri(meth)acrylate, ethylene glycol di(meth)acrylate, polyethylene glycol(meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, Methylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triallylamine, ethylene glycol diglycidyl ether, propylene glycol, glycerin or ethylene carbonate can be used alone, or two or more thereof can be used in combination, but are not limited thereto.

Such internal crosslinking agent may be included in the concentration of about 0.001% to 1% by weight based on the monomer composition. In other words, if the concentration of the internal crosslinking agent is too low, the absorption rate of the polymer is lowered and the gel strength can be reduced, which is not preferable. In contrast, if the concentration of the internal crosslinking agent is too high, the absorptive capacity is lowered and thus it may be not preferable as an absorber.

In addition, the monomer composition may further include additives such as a thickener, a plasticizer, a preservation stabilizer, an antioxidant, and so on, as needed.

Further, the monomer composition may be prepared in the form of a solution in which the raw materials such as the above-mentioned monomer, the polymerization initiator or the internal crosslinking agent are dissolved in a solvent.

In this regard, as the solvent usable herein, any solvent can be used without limitation in the construction as long as it can dissolve the above-described raw materials. For example, as the solvent, water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, N,N-dimethyl acetamide, or mixtures thereof may be used.

Further, the formation of the hydrous gel phase polymer through the polymerization of the monomer composition can be carried out by a conventional polymerization method, and the process thereof is not particularly limited. In a non-limiting example, the polymerization method is largely classified into a thermal polymerization and a photopolymerization depending on the type of the polymerization energy source. The thermal polymerization may be carried out in a reactor like a kneader equipped with agitating spindles, and the photopolymerization may be carried out in a reactor equipped with a movable conveyor belt.

As an example, the thermal polymerization is carried out by injecting the monomer composition into a reactor like a kneader equipped with the agitating spindles and then supplying hot air to the reactor or heating the reactor, thereby obtaining a hydrous gel phase polymer. The hydrous gel phase polymer discharged from the outlet of the reactor may be obtained as a particle with a size of centimeters or millimeters, depending on the type of the agitating spindles equipped in the reactor. Specifically, the hydrous gel phase polymer may be obtained into various shapes depending on the monomer concentration, the injection rate or the like of the monomer composition injected thereto, and the hydrous gel phase polymer having a (weight average) particle diameter of 2 mm to 50 mm can be generally obtained.

Further, as another example, when the photopolymerization of the monomer composition is carried out in a reactor equipped with a movable conveyor belt, the sheet-shaped hydrous gel phase polymer can be obtained. In this case, the thickness of the sheet may vary depending on the concentration and the injection rate of the monomer composition injected thereto. However, typically it is preferable to adjust to a thickness of 0.5 to 5 cm, in order to ensure the production speed or the like while uniformly polymerizing the entire sheet.

The hydrous gel phase polymer obtained by the above-mentioned methods may have typically a moisture content of about 40% to 80% by weight. As used here, the term "moisture content" refers to the content of moisture occupied based on total weight of the hydrous gel phase polymer, and it may be a value calculated by subtracting the weight of the dried polymer from the weight of the hydrous gel phase polymer. Specifically, it may be defined by the value calculated by measuring the weight loss according to evaporation of water in the polymer in the process of raising the temperature of the polymer and drying it through infrared heating. In this case, the drying condition is that the temperature is raised to about 180° C. and then maintaining at 180° C., and thus the total drying time can be set to 20 minutes including the temperature raising step for 5 minutes Step of Passing the Hydrous Gel Phase Polymer Through a Chopper Die and Pulverizing the Polymer (Step 2)

In order to increase the drying efficiency of the hydrogen polymer polymerized in Step 1 and also to affect the morphology of the super absorbent polymer, thus increasing a centrifuge retention capacity (CRC) and an absorbency under load (AUL) of the super absorbent polymer, the present invention includes a step of passing the hydrous gel phase polymer through a chopper die and pulverizing the polymer, prior to drying the hydrogen polymer. In order to distinguish it from the pulverization of the step 4 to be described below, the present disclosure uses the term "coarse pulverization" for convenience.

As used herein, the term "coarse pulverization" means that, when the hydrous gel phase polymer with high water content synthesized in the step 1 is extruded with a chopper die, the hydrous gel phase polymer is pulverized while passing through a plurality of holes equipped in the chopper die. In particular, the chopper die used in the present invention has a plurality of holes and the opening and closing rate of the chopper die is 30 to 40% and the chopper die satisfies the following Mathematical Formula 1:

$$c > 2 \times \sqrt{0.4 \times \pi \times n \times A}$$ [Mathematical Formula 1]

wherein

A is the overall area of the upper surface of the chopper die, n is the number of holes, and c is the total circumference of the plurality of holes.

The opening and closing rate of the chopper die refers to the total area of holes compared to the overall area of the upper surface of the chopper die. For example, for the chopper die provided with n holes having a circular shape where the radius of the chopper die is R and a circular shape where the radius is r, the opening/closing rate is calculated by $n\pi r^2/\pi R^2$. The opening and closing rate of the chopper die is preferably 30 to 40%. If the opening and closing rate is less than 30%, the hydrous gel phase polymer has a large resistance when exiting the holes and thus the chopper die is likely to be damaged. If the opening and closing rate is greater than 40%, the effects of pulverizing the hydrous gel phase polymer is insignificant.

The chopper die used in the present invention satisfies Mathematical Formula 1. In Mathematical Formula 1, c means the total circumference of the plurality of holes, and for example, the c-values of the chopper die provided with n holes having a circular shape where the radius is r is calculated by $n \times 2\pi r$.

The circumference of the holes of chopper die is associated with the contact area with holes of the chopper die when the hydrous gel phase polymer is extruded. The wider the contact area, the hydrous gel phase polymer is effectively pulverized and the surface of the pulverized hydrous gel phase polymer becomes more rough shape while passing through the holes of chopper die, thereby increasing a centrifuge retention capacity (CRC) and an absorbency under load (AUL) of the super absorbent polymer.

Further, the thickness of the chopper die is preferably 5 to 15 mm. If the thickness is less than 5 mm, the chopper die is likely to be broken by the pressure of the extruded hydrous gel phase polymer, and if the thickness is greater than 15 mm, there is a problem that the extrusion resistance of the hydrous gel phase polymer increases.

Also, the c-value of the chopper die is preferably 500 to 800 mm. If the c-value is less than 500 mm, the contact area between the hydrous gel phase polymer and the holes is too small and thus there is a problem that the extrusion resistance increases. If the c-value is greater than 800 mm, there is a problem that the pulverizing effect of the hydrous gel phase polymer is insignificant.

Further, the shape of the holes is not particularly limited within the range satisfying Mathematical Formula 1 and for example, it may be a polygon other than a circle, for example, a star shape or the like. Preferably, in order to obtain an uniform morphology of the hydrous gel phase polymer to be pulverized, the n-holes may have the identical shape with each other.

The hole number (n) is not particularly limited within the range satisfying the Mathematical Formula 1, and for example it may be 10 to 30.

When the hydrous gel phase polymer comes out through chopper die holes, the polymer can be pulverized in a way that the chopper die holes are rotated. The rotation speed is not particularly limited, but it is desirable to adjust the rotation speed so that the particle size of the hydrous gel phase polymer becomes 2 to 10 mm. In other words, in order to increase the drying efficiency, the hydrous gel phase polymer is preferably pulverized into a particle diameter of 10 mm or less. However, upon excessive pulverization, the aggregation phenomenon between particles may occur. Thus, the hydrous gel phase polymer is preferably pulverized into a particle diameter of 2 mm or more.

Further, since the hydrous gel phase polymer is in a state of high water content, a phenomenon where the polymer sticks to the surface of the pulverizing device may occur.

In order to minimize this phenomenon, in the coarsely pulverizing step, fine particle aggregation preventing agents such as steam, water, surfactant, clay or silica; thermal polymerization initiators such as persulfate-based initiators, azo-based initiators, hydrogen peroxide and ascorbic acid, epoxy-based crosslinking agents, diol crosslinking agents, crosslinking agents containing multi-functional groups of di-, tri- or higher functional groups, crosslinking agents such as a compound with mono-functional group including hydroxy group may be used as needed.

Step of Drying the Hydrous Gel Phase Polymer (Step 3)

The method for preparing a super absorbent polymer includes a step of drying the hydrous gel phase polymer formed through the above-mentioned steps.

The drying step may be carried out at a temperature of 120° C. to 250° C., or 150° C. to 200° C., or 160° C. to 180° C. (In this case, the above temperature can be defined as the temperature of a heating medium provided for drying or the internal temperature of drying reactors containing a heating medium and a polymer in the drying step). That is, if the drying temperature is low and the drying time is prolonged, the physical properties of the final polymer may be decreased. Thus, in order to prevent these problems, the drying temperature is preferably 120° C. or higher. Further, if the drying temperature is higher than necessary, only the surface of the hydrous gel phase polymer is dried, and thus a generation amount of fine powders may be increased during the pulverizing step to be described later and the physical properties of the final polymer may be deteriorated. Thus, in order to prevent these problems, the drying temperature is preferably 250° C. or less.

At this time, the drying time for the drying step is not particularly limited, but the drying time may be adjusted to 20 to 90 minutes at the above-mentioned drying temperature range, in consideration of the process efficiency or the like, but it is not limited thereto.

In the drying step, any known drying method may also be used without limitation in the construction if it is a method generally used for the drying process of the hydrous gel phase polymer. Specifically, the drying step may be carried out by a method such as hot air supply, infrared irradiation, microwave irradiation or ultraviolet irradiation.

The polymer dried by the above-described method can exhibit a moisture content of about 0.1% to 10% by weight. In other words, if the moisture content of the polymer is less than 0.1% by weight, it may cause excessively dry and thus production costs may increase and the crosslinked polymer may degrade, which is not advantageous. In addition, if the moisture content is greater than 10% by weight, it is not preferable because a defect may occur in a subsequent step.

Step of Pulverizing the Dried Polymer (Step 4)

The method for preparing a super absorbent polymer includes a step of pulverizing the polymer dried through the above-mentioned steps.

The pulverizing step is a step for optimizing the surface area of the dried polymer, and it can be carried out so that the particle size of the pulverized polymer becomes 150 to 850 μm. Examples of a pulverizing device that can be used to pulverize into the above particle size may include a pin mill, a hammer mill, a screw mill, a roll mill, a disc mill, a jog mill or the like.

In addition, in order to control the physical properties of the super absorbent polymer powder finally manufactured, a step of selectively classifying particles having a particle diameter of 150 μm to 850 μm from the polymer powders obtained through the pulverization can be further carried out.

Step of Surface-Crosslinking the Pulverized Polymer (Step 5)

The method for preparing a super absorbent polymer includes a step of surface-crosslinking the polymer pulverized through the above-mentioned steps.

The surface crosslinking is a step for increasing the crosslinking density near the surface of the polymer particles, and it can be carried out by a method of mixing a solution containing a crosslinking agent (surface crosslinking agent) with the pulverized polymer to perform crosslinking reaction.

Here, the kind of the crosslinking agent (surface crosslinking agent) contained in the surface cross-linking solution is not particularly limited. In a non-limiting example, the surface crosslinking agent may be one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylolpropane, pentaerythritol, sorbitol, calcium hydroxide, magnesium hydroxide, aluminum hydroxide, iron hydroxide, calcium chloride, magnesium chloride, aluminum chloride, and iron chloride.

At this time, the amount of the surface crosslinking agent may be appropriately adjusted depending on the kind of the crosslinking agent or the reaction condition, and preferably can be adjusted to 0.001 to 5 parts by weight based on 100 parts by weight of the pulverized polymer, if the amount of the surface crosslinking agent is too low, the surface crosslink is not properly introduced and the physical properties of the final polymer can be reduced. In contrast, if the surface crosslinking agent is used in an excessively large amount, the absorptive capacity of the polymer may be lowered due to excessive surface crosslinking reaction, which is not desirable.

On the other hand, in order to carry out the surface crosslinking step, a method of adding the surface crosslinking solution and the pulverized polymer to a reaction tank and then mixing them, a method of spraying the surface crosslinking solution onto the pulverized polymer, a method of continuously supplying the pulverized polymer and the surface crosslinking solution to a mixer being continuously operated and then mixing them, and the like can be used.

Then, when the surface crosslinking solution is added, water may be further added. Thus, by adding water together, more uniform dispersion of the crosslinking agent can be induced, the aggregation phenomenon of the polymer powder can be prevented, and the penetration depth of the surface crosslinking agent for the polymer powder can be more optimized. In consideration of these objects and advantages, the amount of water to be added can be adjusted within the range of 0.5 to 10 parts by weight relative to 100 parts by weight of the pulverized polymer.

Then, the surface crosslinking step may be carried out at a temperature of 100 to 250° C., and it can be continuously made after the drying and pulverizing steps being conducted at a relatively high temperature. At this time, the surface crosslinking reaction can be carried out for 1 to 120 minutes, or 1 to 100 minutes, or 10 to 60 minutes. That is, in order to prevent the polymer particles from being damaged due to excessive surface reaction to lead to deterioration in the physical properties, while inducing surface crosslinking reaction to the minimum, the surface crosslinking can be carried out under the above-described reaction conditions.

By using these methods, a super absorbent polymer having less generation amount of coarse particles and fine particles, excellent absorption properties such as a centrifuge retention capacity and an absorbency under load, and improved permeability can be prepared.

Advantageous Effects

The super absorbent polymer and the method for preparing the same according to the present invention have features that it is possible to prepare a super absorbent polymer that can have an improved centrifuge retention capacity (CRC) and a high absorbency under load (AUL) by controlling the shape and size of the chopper die holes during coarse pulverization of a hydrous gel phase polymer.

BRIEF DESCRIPTION OF DRAWINGS

FIGS. 1 to 3 illustrate the chopper dies used in an example of the present invention, respectively.

FIGS. 4 and 5 illustrate the chopper dies used in a comparative example of the present invention, respectively.

FIG. 6 represents a SEM image of the surface of the absorbent polymer prepared an example and a comparative example of the present invention. FIG. 6(a) to FIG. 6(d) represent the absorbent polymers prepared in Comparative Example 1, Example 1, Example 2 and Example 3, respectively.

DETAILED DESCRIPTION OF THE EMBODIMENTS

Hereinafter, the preferred Examples are provided for better understanding. However, these Examples are given for illustrative purposes only and the invention are not intended to be limited by these Examples.

EXAMPLE 1

20 g of PEGDA (polyethyleneglycol diacrylate) and 14 g of ETTA (trimethylolpropane triacrylate) as the internal crosslinking agent were mixed with 490 g of acrylic acid, followed by mixing with 80 ppm of a photoinitiator (Irgacure 819). 670 g of 32% aqueous sodium hydroxide solution was added to the mixture to prepare a acrylic acid monomer composition with a neutralization degree of 70 mol %. The monomer composition was sufficiently stirred while maintaining at 42±1° C. Polymerization was initiated after about 30 seconds, and the resulting gel was divided by applying a shear force to the gel for 5 minutes to which 260 g of water was then added to prepare a gel. The gel thus prepared was coarsely pulverized for about 5 minutes, and the chopper dies (FIG. 1) used in the coarse pulverization were as follows.
Diameter of a chopper die: 81 mm
Thickness of a chopper die: 10 mm
Center hole of a chopper die: 18.5 mm
Diameter of the side groove of a chopper die: 2.5 mm
Shape of holes: shamrock shape
Number of holes: 10
Total circumference of holes: 550 mm
(wherein the center hole of the chopper die is connected with spindles for rotating the chopper die, and the following Examples and Comparative Examples are likewise).
1 kg of the coarsely pulverized gel was evenly spread on the dryer and dried. Drying was divided into a total of nine zones, among which the initial three zones were dried at a temperature of 185° C. and the remaining zones were dried at a temperature of 180° C., the respective zones being proceeded for about 4 to 5 minutes. The drying was carried out by setting the direction of the drying air four times from bottom to top and five times from top to bottom, and thus the drying was carried out for a total of 41 minutes. The dried polymer was pulverized by using a pulverizing device and size-classified through a standard mesh sieve according to ASTM standard to obtain an absorbent polymer powder having a particle size of 150 to 850 μm.

To 50 g of the resulting polymer powder, the surface crosslinking solution containing 0.4 g of ethylene carbonate as a surface crosslinking agent, 3.5 g of methanol; 3 g of water and 0.1 g of silica (Aerosil 380) was added and uniformly mixed, followed by drying in a hot air oven at 190° C. for 40 minutes. The dried powder was size-classified through a standard mesh sieve according to ASTM standard to obtain a super absorbent polymer having a particle size of 150 to 850 μm.

EXAMPLE 2

The super absorbent polymer was prepared in the same manner as in Example 1, with the exception that the following chopper dies (FIG. 2) were used.
Diameter of a chopper die: 81 mm
Thickness of a chopper die: 10 mm
Center hole of a chopper die: 18.5 mm
Diameter of the side groove of a chopper die: 2.5 mm
Shape of holes: star shape
Number of holes: 10
Total circumference of holes: 650 mm

EXAMPLE 3

The super absorbent polymer was prepared in the same manner as in Example 1, with the exception that the following chopper dies (FIG. 3) were used.
Diameter of a chopper die: 81 mm
Thickness of a chopper die: 10 mm
Center hole of a chopper die: 18.5 mm
Diameter of the side groove of a chopper die: 2.5 mm
Shape of holes: banana shape
Number of holes: 10
Total circumference of holes: 640 mm

EXAMPLE 4

The super absorbent polymer was prepared in the same manner as in Example 2, with the exception that the surface crosslinking solution containing 0.3 g of 1,3-propane diol as a surface crosslinking agent, 3 g of methanol, 3 g of water and 0.1 g of silica (Aerosil 200) was used.

EXAMPLE 5

The super absorbent polymer was prepared in the same manner as in Example 3, with the exception that the surface crosslinking solution containing 0.3 g of 1,3-propane diol as a surface crosslinking agent, 3 g of methanol, 3 g of water and 0.1 g of silica (Aerosil 200) was used.

COMPARATIVE EXAMPLE 1

The super absorbent polymer was prepared in the same manner as in Example 1 with the exception that the following chopper dies (FIG. 4) were used.
Diameter of a chopper die: 81 mm
Thickness of a chopper die: 10 mm
Shape of holes: circular shape with a diameter of 14 mm Center hole of a chopper die: 18.5 mm
Diameter of the side groove of a chopper die: 2.5 mm
Number of holes: 10
Total circumference of holes: 440 mm

COMPARATIVE EXAMPLE 2

The super absorbent polymer was prepared in the same manner as in Example 1, with the exception that the following chopper dies (FIG. 5) were used.
Diameter of a chopper die: 81 mm
Thickness of a chopper die: 10 mm
Cater hole of a chopper die: 18.5 mm
Diameter of the side groove of a chopper die: 2.5 mm
Shape of holes: circular shape with a diameter of 8 mm
Number of holes: 34
Total circumference of holes: 854 mm

EXPERIMENTAL EXAMPLE 1

1) Ratio of the Absorbency Under Load at 5 Minutes to the Absorbency Under Load at 60 Minutes (ARUL)

ARUL (absorbing rate under load) was measured for the super absorbent polymers prepared in the Examples and Comparative Examples according to the following Equation:

$$ARUL = 0.3AUL(5\ min)/0.3AUL(60\ min) \quad [\text{Equation 1}]$$

in Equation 1, 0.3AUL (5 min) and 0.3AUL (60 min) are the values of absorbency under load (AUL) at 5 minutes and 60 minutes shown in the following Equation 2, respectively, $$0.3AUL(g/g) = [Wb(g) - Wa(g)]/\text{mass}(g)\ \text{of the absorbent polymer} \quad [\text{Equation 2}]$$

in Equation 2, $Wa(g)$ is the sum of the weight of the absorbent polymer and the weight of the device capable of providing a load for the absorbent polymer, and $Wb(g)$ is the sum of the weight of the absorbent polymer in which moisture is absorbed after supplying water for the absorbent polymer under a load (0.3 psi) for 5 minutes or 1 hour, and the weight of the device capable of providing a load for the absorbent polymer.

In this case, the absorbency under load was measured according to the EDANA WSP 242.2 method.

A 400 mesh stainless steel net was installed in the bottom of a plastic cylinder having an internal diameter of 60 mm. 0.9 g of the absorbent polymer was uniformly scattered on the steel net at the room temperature and the humidity of 50%, and a piston which can provide a load of 0.3 psi uniformly was put thereon. The external diameter of the piston was slightly smaller than 60 mm, there was no gap between the internal wall of the cylinder and the piston, and the jig-jog of the cylinder was not interrupted. In this regard, the weight Wa(g) of the device was measured.

After putting a glass filter having a diameter of 90 mm and a thickness of 5 mm in a Petri dish having a diameter of 150 mm, a physiological saline solution composed of 0.9 wt % of sodium chloride was poured in the dish until the surface level became equal to the upper surface of the glass filter. A sheet of filter paper having a diameter of 90 mm was put thereon. The measuring device was put on the filter paper and the solution was absorbed under a load. After 5 minutes and 1 hour, the weight Wb(g) was measured after lifting the measuring device up. 0.3AUL (5 min) and 0.3AUL (60 min) were calculated from the above measured results, respectively.

The measured results are shown in Table 1 below.

2) Absorbency Under Load (0.9AUL (60 Min))

The absorbency under load (0.9AUL (60 min)) was measured for the absorbent polymers prepared in the Examples and Comparative Examples according to the following Equation 3:

$$0.9AUL(g/g) = [Wb(g) - Wa(g)]/\text{weight}(g)\ \text{of the absorbent polymer} \quad [\text{Equation 3}]$$

in Equation 3, $Wa(g)$ is the sum of the weight of the absorbent polymer and the weight of the device capable of providing a load for the absorbent polymer, and $Wb(g)$ is the sum of the weight of the absorbent polymer in which moisture is absorbed after supplying water for the absorbent polymer under a load (0.9 psi) for 1 hour, and the weight of the device capable of providing a load for the absorbent polymer.

In this case, the absorbency under load was measured according to the EDANA WSP 242.2 method, and this was measured in the same manner in the previous 0.3AUL (60 min), with the exception that a piston capable of uniformly further providing a load of 0.9 psi.

3) CRC(Centrifuge Retention Capacity)

The CRC of the absorbent polymers prepared in Examples and Comparative Examples was evaluated by the following method.

In accordance with EDANA WSP 241.2 (European Disposables and Nonwovens Association, EDANA), the retention capacity by absorbency under no load was measured for the absorbent polymers prepared in Examples and Comparative Examples.

Specifically, the polymer $W_0$ (g, about 0.2 g) prepared in Examples and Comparative Examples was uniformly put in a nonwoven fabric-made bag, followed by sealing. Then, the bag was immersed in 0.9 wt % of a physiological saline solution at room temperature. After 30 minutes, moisture was removed from the bag at 250 G for 3 minutes with a centrifuge, and the weight $W_2(g)$ of the bag was then measured. Further, the same procedure was carried out without using the polymer, and then the resultant weight $W_1(g)$ was measured. Thus, CRC (g/g) was calculated from the respective weights thus obtained, according to the following Equation.

$$CRC(g/g) = \{[W_2(g) - W_1(g)]/W_0(g)\} - 1 \quad [\text{Equation 4}]$$

in Equation 4, $W_0(g)$ is a weight (g) of the absorbent polymer, $W_1(g)$ is a weight (g) of the device which is measured after draining water off at 250 G for 3 minutes with a centrifuge, without using the absorbent polymer, and $W_2(g)$ is a weight (g) of the device including the absorbent polymer, which is measured after immersing the absorbent polymer in 0.9% by weight of the physiological saline solution at room temperature for 30 minutes and then draining water off at 250 G for 3 minutes with a centrifuge.

The results thus obtained are shown in Table 1 below. For comparison, the loads (ampere) of the pulverizing device when pulverizing with chopper dies in Examples and Comparative Examples are also shown together.

TABLE 1

| | CRC (g/g) | | ARUL (%) | | 0.9AUL (60 min) | | | |
|---|---|---|---|---|---|---|---|---|
| | Before surface crosslinking | After surface crosslinking | Before surface crosslinking | After surface crosslinking | (g/g) After surface crosslinking | Ampere (A) | | |
| | | | | | | min | max | Average |
| Ex. 1 | 38.9 | 30.7 | 35.5 | 61.3 | 18.0 | — | — | — |
| Ex. 2 | 39.3 | 31.1 | 40.3 | 71.4 | 19.1 | 1.6 | 2.6 | 2.1 |
| Ex. 3 | 41.4 | 31.6 | 42.2 | 69.8 | 18.5 | 1.7 | 2.5 | 2.1 |
| Ex. 4 | 39.4 | 31.0 | 40.5 | 70.5 | 19.0 | 1.6 | 2.6 | 2.1 |
| Ex. 5 | 40.2 | 31.2 | 39.9 | 70.3 | 18.7 | 1.5 | 2.6 | 2.0 |
| Com. Ex. 1 | 39.6 | 31.4 | 39.5 | 53.9 | 17.5 | — | — | — |
| Com. Ex. 2 | 39.5 | 31.8 | 39.7 | 70.0 | 17.7 | 1.8 | 3.0 | 2.4 |

As shown in Table 1, it could be confirmed that the absorbency under load (0.9AUL) of Examples was excellent as compared to Comparative Examples. In addition, ARUL of Examples was significantly excellent as compared to Comparative Examples, and Comparative Example 2 exhibited the same level of ARUL as Examples, but since the load applied to the chopper die was high, it was difficult to apply to the actual process.

EXPERIMENTAL EXAMPLE 2

The morphology of the super absorbent polymer prepared in Examples and Comparative Examples was confirmed by SEM image, and the results are shown in FIG. 6.

As shown in FIG. 6, it could be confirmed that the surface of the super absorbent polymer of Examples became more rough form than that of Comparative Examples, thereby increasing the centrifuge retention capacity (CRC) and the absorbency under load (AUL) of the super absorbent polymer.

The invention claimed is:

1. A method of preparing a superabsorbent polymer comprising:
   1) carrying out thermal polymerization or photopolymerization of a monomer composition including a water-soluble ethylene-based unsaturated monomer and a polymerization initiator to form a hydrous gel phase polymer;
   2) passing the hydrous gel phase polymer through a chopper die and pulverizing the polymer;
   3) drying the pulverized hydrous gel phase polymer;
   4) pulverizing the dried polymer; and
   5) surface-crosslinking the pulverized polymer,
   wherein the chopper die is provided with a plurality of non-circular holes,
   the chopper die has an opening/ closing rate of 30 to 40%, and
   the chopper die satisfies the following Mathematical Formula 1:

$$c > 2 \times \sqrt{0.4 \times \pi \times n \times A}$$ [Mathematical Formula 1]

wherein
   A is the overall area of the upper surface of the chopper die with a unit mm$^2$, n is the number of holes, and c is the total circumference of the plurality of holes, and wherein the value of c is 500 to 800 mm.

2. The method of claim 1, wherein the thickness of the chopper die is 5 to 15 mm.

3. The method of claim 1, wherein the n-holes have the identical shape with each other.

4. The method of claim 1, wherein n is an integer of 10 to 30.

5. The method of claim 1, wherein the pulverizing in step 2) is a step of pulverizing the hydrous gel phase polymer into a particle size of 2 to 10 mm.

6. The method of claim 1, wherein
   the drying in step 3) is carried out at a temperature of 120 to 250° C.

7. The method of claim 1, wherein
   the pulverizing in step 4) is carried out so that the particle size of the pulverized polymer becomes 150 to 850 µm.

8. The method of claim 1, wherein the surface-crosslinking in Step 5) is carried out at a temperature of 100 to 250° C.

9. The method of claim 1, wherein
   the water-soluble ethylene-based unsaturated monomer is a compound represented by the following Chemical Formula 1:

$$R_1\text{—COOM}^1$$ [Chemical Formula 1]

in Chemical Formula 1,
   $R_1$ is a $C_2$-$C_5$ alkyl group including an unsaturated bond, and
   $M^1$ is a hydrogen atom, a monovalent or divalent metal, an ammonium group, or an organic amine salt.

10. The method of claim 1, wherein
    the water-soluble ethylene-based unsaturated monomer includes one or more selected from the group consisting of: acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, 2-(meth)acrylamide-2-methyl propane sulfonic acid, (meth)acrylamide, N- substituted (meth)acrylate, 2-hydroxyethyl(meth)acrylate, 2-hydroxypropyl(meth)acrylate, methoxy polyethylene glycol (meth)acrylate, polyethylene glycol (meth)acrylate,(N,N)-dimethylaminoethyl (meth)acrylate, and (N,N)-dimethylaminopropyl(meth) acrylamide.

11. The method of claim 1, wherein
    the surface crosslinking is carried out by reacting one or more crosslinking agents selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylolpropane, pentaerythritol, sorbitol, calcium hydroxide, magnesium hydroxide, aluminum hydroxide, iron hydroxide, calcium chloride, magnesium chloride, aluminum chloride, and iron chloride.

* * * * *